(12) United States Patent
Liu et al.

(10) Patent No.: US 9,108,895 B2
(45) Date of Patent: Aug. 18, 2015

(54) PROMOTED RUTHENIUM CATALYST FOR THE IMPROVED HYDROGENATION OF CARBOXYLIC ACIDS TO THE CORRESPONDING ALCOHOLS

(71) Applicant: Eastman Chemical Company, Kingsport, TN (US)

(72) Inventors: Zhufang Liu, Kingsport, TN (US); Brent Alan Tennant, Church Hill, TN (US); Jerome Leonard Stavinoha, Jr., Longview, TX (US); Anthony Dominick Messina, Kingsport, TN (US); Noah Glenn McMillan, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 223 days.

(21) Appl. No.: 13/661,088

(22) Filed: Oct. 26, 2012

(65) Prior Publication Data

US 2014/0121400 A1    May 1, 2014

(51) Int. Cl.
*C07C 27/04*    (2006.01)
*C07C 29/149*    (2006.01)

(52) U.S. Cl.
CPC .................... *C07C 29/149* (2013.01)

(58) Field of Classification Search
CPC .................................... C07C 29/149
USPC .......................................... 568/885
See application file for complete search history.

(56) References Cited

U.S. PATENT DOCUMENTS

| | | |
|---|---|---|
| 1,839,974 A | 1/1932 | Lazier |
| 2,607,807 A | 8/1952 | Ford |
| 4,104,478 A | 8/1978 | Trivedi |
| 4,214,106 A | 7/1980 | Freudenberger et al. |
| 4,218,401 A | 8/1980 | Wymore |
| 4,317,918 A | 3/1982 | Takano et al. |
| 4,338,221 A | 7/1982 | Qualeatti |
| 4,480,115 A | 10/1984 | McGinnis |
| 4,490,482 A | 12/1984 | Mathieu |
| 4,524,225 A | 6/1985 | Qualeatti et al. |
| 4,611,085 A | 9/1986 | Kitson |
| 4,659,686 A | 4/1987 | Griffiths et al. |
| 4,777,303 A | 10/1988 | Kitson et al. |
| 4,804,791 A | 2/1989 | Kitson et al. |
| 4,826,795 A | 5/1989 | Kitson et al. |
| 4,880,937 A | 11/1989 | Matsushita et al. |
| 4,973,717 A | 11/1990 | Williams |
| 4,985,572 A | 1/1991 | Kitson et al. |
| 4,990,655 A | 2/1991 | Kitson et al. |
| 5,061,671 A | 10/1991 | Kitson et al. |
| 5,089,453 A | 2/1992 | Wilson et al. |
| 5,149,680 A | 9/1992 | Kitson et al. |
| 5,334,769 A | 8/1994 | Ferrero et al. |
| 5,393,919 A | 2/1995 | Shinoda |
| 5,395,990 A | 3/1995 | Scarlett |
| 5,395,991 A | 3/1995 | Scarlett et al. |
| 5,426,246 A | 6/1995 | Nagahara et al. |
| 5,476,827 A | 12/1995 | Ferrero et al. |
| 5,478,952 A | 12/1995 | Schwartz |
| 5,496,786 A | 3/1996 | Gubitosa et al. |
| 5,731,479 A | 3/1998 | Antons |
| 5,973,210 A | 10/1999 | Jacquot et al. |
| 5,985,789 A | 11/1999 | Tooley et al. |
| 6,008,384 A | 12/1999 | Bockrath et al. |
| 6,043,187 A | 3/2000 | Harle et al. |
| 6,140,545 A | 10/2000 | Merger et al. |
| 6,180,830 B1 | 1/2001 | Jacquot |
| 6,204,417 B1 | 3/2001 | Fischer et al. |
| 6,284,932 B1 | 9/2001 | Fischer et al. |
| 6,355,848 B1 | 3/2002 | Antons et al. |
| 6,376,414 B1 | 4/2002 | Antons et al. |
| 6,387,248 B2 | 5/2002 | Sherwood, Jr. et al. |
| 6,403,844 B1 | 6/2002 | Zhang et al. |
| 6,429,167 B1 | 8/2002 | Maeno et al. |
| 6,486,367 B1 | 11/2002 | Budge et al. |
| 6,495,730 B1 * | 12/2002 | Konishi et al. ............... 568/831 |
| 6,566,539 B1 | 5/2003 | Campos et al. |
| 6,670,490 B1 | 12/2003 | Campos et al. |
| 6,706,932 B1 | 3/2004 | Konishi et al. |
| 7,045,479 B2 | 5/2006 | Zhou et al. |
| 7,119,045 B2 | 10/2006 | Magna et al. |
| 7,126,034 B2 | 10/2006 | Meng et al. |
| 7,419,928 B2 | 9/2008 | Malek et al. |
| 7,507,866 B2 | 3/2009 | Urtel et al. |
| 7,863,489 B2 | 1/2011 | Johnston et al. |
| 7,989,664 B2 | 8/2011 | Cortright |

(Continued)

FOREIGN PATENT DOCUMENTS

| | | |
|---|---|---|
| EP | 1 232 789 A1 | 8/2002 |
| EP | 1 757 571 A1 | 2/2007 |

(Continued)

OTHER PUBLICATIONS

PCT International Search Report and Written Opinion dated Jan. 27, 2014 for International Application No. PCT/US2013/064450.

(Continued)

*Primary Examiner* — Porfirio Nazario Gonzalez
*Assistant Examiner* — Kofi Adzamli
(74) *Attorney, Agent, or Firm* — Tammye L. Taylor; Louis N. Moreno

(57) ABSTRACT

The invention relates to ruthenium-rhenium-tin and ruthenium-rhenium catalysts effective for the reduction of carboxylic acids to the corresponding alcohols and processes for the reduction of carboxylic acids to the corresponding alcohols using the ruthenium-rhenium-tin and ruthenium-rhenium catalysts.

20 Claims, 4 Drawing Sheets

(56) References Cited

U.S. PATENT DOCUMENTS

| | | |
|---|---|---|
| 8,013,193 B2 | 9/2011 | Maeda et al. |
| 2010/0317901 A1 | 12/2010 | Chaudhari et al. |
| 2011/0082322 A1 | 4/2011 | Jevtic et al. |

FOREIGN PATENT DOCUMENTS

| | | |
|---|---|---|
| JP | 9025253 A | 1/1997 |
| JP | 9234368 A | 9/1997 |
| JP | 9241192 A | 9/1997 |
| JP | 2003 024791 A | 1/2003 |
| WO | WO 2007/065891 A1 | 6/2007 |

OTHER PUBLICATIONS

Echeverri, David A., et al.; "Characterization and carbonylic hydrogenation of methyl oleate over Ru—Sn/$Al_2O_3$: Effects of metal precursor and chlorine removal"; Applied Catalysis A: General 366; 2009; pp. 342-347.

Hara, Yoshinori, et al.; "The drastic effect of platinum on carbon-supported ruthenium-tin catalysts used for hydrogenation reactions of carboxylic acids"; Applied Catalysis A: General 239; 2003; pp. 181-195.

He, De-Hua, et al.; "Hydrogenation of Carboxylic Acids Using Bimetallic Catalysts Consisting of Group 8 to 10, and Group 6 or 7 Metals"; Tetrahedron Letters, vol. 36, No. 7; pp. 1059-1062; 1995.

Kikuchi, Ryuji, et al.; "Hydrogenation of ethyl phenylacetate to 2-phenylethanol by ruthenium/tin/alumina catalysts Elimination of need for high temperature activation of the catalysts with hydrogen; optimum oxidation state of tin"; Applied Catalysis A: General 165; 1997; pp. 309-317.

Kluson, Petr, et al.; "Selective hydrogenation over ruthenium catalysts"; Applied Catalysis A: General 128; 1995, pp. 13-31.

Mendes, M. J., et al.; "Hydrogenation of oleic acid over ruthenium catalysts"; Applied Catalysis A: General 217; 2001; pp. 253-262.

Tahara, Katsuhiko, et al.; "Liquid-phase hydrogenation of dicarboxylates catalyzed by supported Ru—Sn catalysts"; Catalysis Today 28; 1996; pp. 267-272.

Tale, R. H., et al.; "An extremely simple, convenient and mild one-pot reduction of carboxylic acids to alcohols using 3,4,5-trifluorophenylboronic acid and sodium borohydride"; Tetrahedron Letters 44; 2003; pp. 3427-3428.

* cited by examiner

PROMOTED RUTHENIUM CATALYST FOR THE IMPROVED HYDROGENATION OF CARBOXYLIC ACIDS TO THE CORRESPONDING ALCOHOLS

FIELD OF THE INVENTION

The present invention relates to catalysts for reduction of carboxylic acids to the corresponding alcohols and methods of reduction of carboxylic acids to the corresponding alcohols. More particularly, the present invention relates to heterogeneous catalysts including ruthenium and rhenium or ruthenium, rhenium and tin for the reduction of carboxylic acids to the corresponding alcohols.

BACKGROUND OF THE INVENTION

Carboxylic acids are notoriously difficult substrates for direct hydrogenation to the corresponding alcohols using heterogeneous hydrogenation catalysts. Standard metals (e.g. Pt, Pd, Ni) used in hydrogenation catalysts are relatively inactive for hydrogenation of carboxylic acids or else require very high temperatures and pressures. Ruthenium has been known for some time to have reasonable activity for the hydrogenation of carboxylic acids to the corresponding alcohols. However, observed hydrogenation rates are still very slow, especially compared to other carbonyl-containing species such as ketones and aldehydes. There is interest in developing new catalysts that are faster and more effective than ruthenium alone for carboxylic acid hydrogenation at mild conditions to form the corresponding alcohol.

BRIEF SUMMARY OF THE INVENTION

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst comprising:
(a) an inert support,
(b) 0.5 to 2.0 weight % ruthenium,
(c) 0.5 to 3.0 weight % rhenium, and
(d) 0.01 to 0.03 weight % tin,
wherein the ratio of the weight % of tin to the weight % of rhenium ranges from 0.01 to 0.50, and
wherein the weight % is based on the total weight of the catalyst.

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst comprising:
(a) an inert support,
(b) 0.5 to 2.0 weight % ruthenium,
(c) 0.5 to 3.0 weight % rhenium, and
(d) 0.01 to 0.03 weight % tin,
wherein the ratio of the weight % of tin to the weight % of rhenium ranges from 0.05 to 0.10, and
wherein the weight % is based on the total weight of the catalyst.

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst comprising:
(a) an inert support,
(b) 0.5 to 2.0 weight % ruthenium,
(c) 0.5 to 3.0 weight % rhenium, and
wherein the weight % is based on the total weight of the catalyst.

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst consisting essentially of:
(a) an inert support,
(b) 0.5 to 2.0 weight % ruthenium,
(c) 0.5 to 3.0 weight % rhenium, and
(d) 0.01 to 0.03 weight % tin,
wherein the ratio of the weight % of tin to the weight % of rhenium ranges from 0.01 to 0.50, and
wherein the weight % is based on the total weight of the catalyst.

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst consisting essentially of:
(a) an inert support,
(b) 0.5 to 2.0 weight % ruthenium,
(c) 0.5 to 3.0 weight % rhenium, and
(d) 0.01 to 0.03 weight % tin,
wherein the ratio of the weight % of tin to the weight % of rhenium ranges from 0.05 to 0.10, and
wherein the weight % is based on the total weight of the catalyst.

In one aspect the present invention provides an anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, wherein the catalyst consists essentially of:
(a) an inert support,
(b) 0.5 to 2.0 weight % ruthenium,
(c) 0.5 to 3.0 weight % rhenium, and
wherein the weight % is based on the total weight of the catalyst.

In one aspect the present invention provides a process comprising a solvent selected from the group consisting ketones, esters, hydrocarbons, alcohols or mixtures thereof.

In one aspect the present invention provides process comprising a solvent that is inert to hydrogenation.

In one aspect the present invention provides a process comprising a solvent that forms a hydroxyl containing compound.

In one aspect the present invention provides a process comprising an inert support of carbon, silica, alumina or mixtures thereof.

In one aspect the present invention provides a process wherein a portion of the alcohol is recycled to the hydrogenation process.

In one aspect the present invention provides a process comprising a support excluding high surface area graphitized carbon.

In one aspect the present invention provides a process comprising a support excluding carbon activated by using a Lewis acid.

In one aspect the present invention provides a hydrogenation catalyst comprising an inert support, 0.5 to 2.0 weight % ruthenium, 0.5 to 3.0 weight % rhenium, and 0.01 to 0.03 weight % tin, wherein the weight % is based on the total weight of the catalyst, and wherein the ratio of the weight % of tin to the weight % of rhenium ranges from 0.01 to 0.50.

In one aspect the present invention provides a hydrogenation catalyst comprising an inert support, 0.5 to 2.0 weight % ruthenium, 0.5 to 3.0 weight % rhenium, and 0.01 to 0.03 weight % tin, wherein the weight % is based on the total weight of the catalyst, and wherein the ratio of the weight % of tin to the weight % of rhenium ranges from 0.05 to 0.10.

In one aspect the present invention provides a hydrogenation catalyst comprising an inert support, 0.5 to 2.0 weight % ruthenium and 0.5 to 3.0 weight % rhenium, wherein the weight % is based on the total weight of the catalyst.

DETAILED DESCRIPTION

Figure 1:
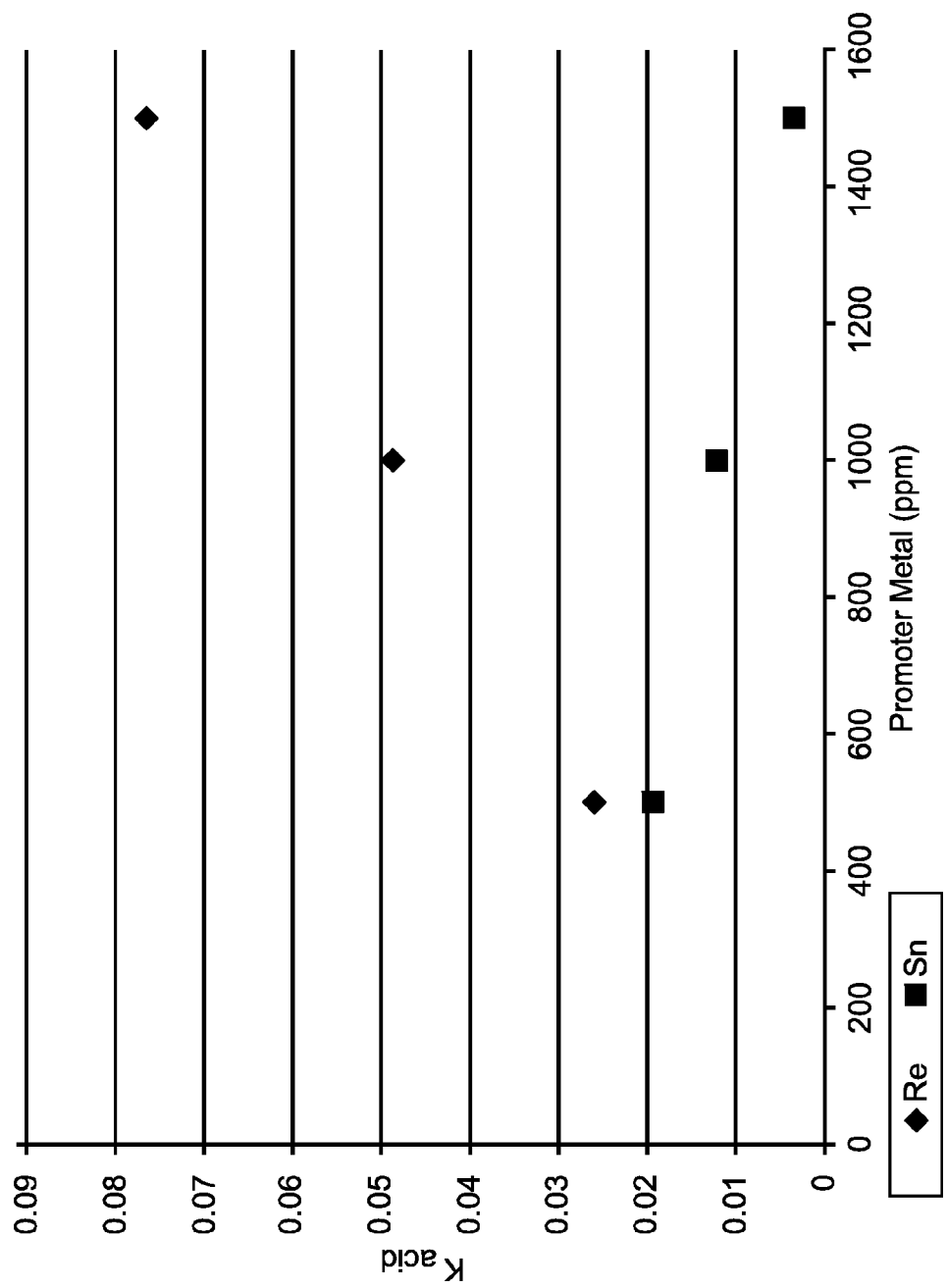
FIG. 1 is a graph showing the effect of Re and Sn as Ru promoters on carboxylic acid hydrogenation rate.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, each numerical parameter should at least be construed in light of the number of reported significant digits and by applying ordinary rounding techniques. Further, the ranges stated in this disclosure and the claims are intended to include the entire range specifically and not just the endpoint(s). For example, a range stated to be 0 to 10 is intended to disclose all whole numbers between 0 and 10 such as, for example 1, 2, 3, 4, etc., all fractional numbers between 0 and 10, for example 1.5, 2.3, 4.57, 6.1113, etc., and the endpoints 0 and 10. Also, a range associated with chemical substituent groups such as, for example, "C1 to C5 hydrocarbons," is intended to specifically include and disclose C1 and C5 hydrocarbons as well as C2, C3, and C4 hydrocarbons.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

As used in the specification and the claims, the singular forms "a," "an" and "the" include their plural referents unless the context clearly dictates otherwise. For example, reference to a "support or a "reactor" is intended to include the one or more supports or reactors. References to a composition or process containing or including "an" ingredient or "a" step is intended to include other ingredients or other steps, respectively, in addition to the one named.

The terms "containing" or "including," are synonymous with the term "comprising," and is intended to mean that at least the named compound, element, particle, or method step, etc., is present in the composition or article or method, but does not exclude the presence of other compounds, catalysts, materials, particles, method steps, etc., even if the other such compounds, material, particles, method steps, etc., have the same function as what is named, unless expressly excluded in the claims. The term "anhydrous" means less than 20 weight % water or less than 10 weight % water or less than 5 weight % water or less than 1 weight % water.

It is also to be understood that the mention of one or more method steps does not preclude the presence of additional method steps before or after the combined recited steps or intervening method steps between those steps expressly identified. Moreover, the lettering of process steps or ingredients is a convenient means for identifying discrete activities or ingredients and the recited lettering can be arranged in any sequence, unless otherwise indicated.

In certain embodiments of the present invention the hydrogenation is catalyzed by a catalyst comprising an inert support, 0.5 to 2.0 weight % ruthenium, 0.5 to 3.0 weight % rhenium, and 0.01 to 3.0 weight % tin, wherein the ratio of weight % of tin to the weight % of rhenium ranges from 0.01 to 0.50 and wherein the weight % is based on the total weight of the catalyst. Alternatively, the hydrogenation is catalyzed by a catalyst consisting essentially of an inert support, 0.5 to 2.0 weight % ruthenium, 0.5 to 3.0 weight % rhenium, and 0.01 to 3.0 weight % tin, wherein the ratio of the weight % of tin to the weight % of rhenium ranges from 0.01 to 0.50 and wherein the weight % is based on the total weight of the catalyst.

In certain embodiments of the present invention the hydrogenation is catalyzed by a catalyst comprising an inert support, 0.5 to 2.0 weight % ruthenium, 0.5 to 3.0 weight % rhenium, and 0.01 to 3.0 weight % tin, wherein the ratio of weight % of tin to the weight % of rhenium ranges from 0.05 to 0.10 and wherein the weight % is based on the total weight of the catalyst. Alternatively, the hydrogenation is catalyzed by a catalyst consisting essentially of an inert support, 0.5 to 2.0 weight % ruthenium, 0.5 to 3.0 weight % rhenium, and 0.01 to 3.0 weight % tin, wherein the ratio of the weight % of tin to the weight % of rhenium ranges from 0.05 to 0.10 and wherein the weight % is based on the total weight of the catalyst.

In certain embodiments of the present invention the hydrogenation is catalyzed by a catalyst comprising an inert support, 0.5 to 2.0 weight % ruthenium, 0.5 to 3.0 weight % rhenium, and 0.01 to 0.03 weight % tin, wherein the ratio of the weight % of tin to the weight % of rhenium ranges from 0.01 to 0.50 and wherein the weight % is based on the total weight of the catalyst. Alternatively, the hydrogenation is catalyzed by a catalyst consisting essentially of an inert support, 0.5 to 2.0 weight % ruthenium, 0.5 to 3.0 weight % rhenium, and 0.01 to 0.03 weight % tin, wherein the ratio of the weight % of tin to the weight % of rhenium ranges from 0.01 to 0.50 and wherein the weight % is based on the total weight of the catalyst.

In certain embodiments of the present invention the hydrogenation is catalyzed by a catalyst comprising an inert support, 0.5 to 2.0 weight % ruthenium, 0.5 to 3.0 weight % rhenium, and 0.01 to 0.03 weight % tin, wherein the ratio of the weight % of tin to the weight % of rhenium ranges from 0.05 to 0.10 and wherein the weight % is based on the total weight of the catalyst. Alternatively, the hydrogenation is catalyzed by a catalyst consisting essentially of an inert support, 0.5 to 2.0 weight % ruthenium, 0.5 to 3.0 weight % rhenium, and 0.01 to 0.03 weight % tin, wherein the ratio of the weight % of tin to the weight % of rhenium ranges from 0.05 to 0.10 and wherein the weight % is based on the total weight of the catalyst.

In certain embodiments of the present invention the hydrogenation is catalyzed by a catalyst comprising an inert support, 0.5 to 2.0 weight % ruthenium, 0.5 to 2.0 weight % rhenium, and 0.01 to 0.03 weight % tin, wherein the ratio of the weight % of tin to the weight % of rhenium ranges from 0.01 to 0.50 and wherein the weight % is based on the total weight of the catalyst. Alternatively, the hydrogenation is catalyzed by a catalyst consisting essentially of an inert support, 0.5 to 2.0 weight % ruthenium, 0.5 to 2.0 weight % rhenium, and 0.01 to 0.03 weight % tin, wherein the ratio of the weight % of tin to the weight % of rhenium ranges from 0.01 to 0.50 and wherein the weight % is based on the total weight of the catalyst.

In certain embodiments of the present invention the hydrogenation is catalyzed by a catalyst comprising an inert support, 0.5 to 2.0 weight % ruthenium, 0.5 to 2.0 weight % rhenium, and 0.01 to 0.03 weight % tin, wherein the ratio of the weight % of tin to the weight % of rhenium ranges from 0.05 to 0.10 and wherein the weight % is based on the total weight of the catalyst. Alternatively, the hydrogenation is catalyzed by a catalyst consisting essentially of an inert support, 0.5 to 2.0 weight % ruthenium, 0.5 to 2.0 weight % rhenium, and 0.01 to 0.03 weight % tin, wherein the ratio of the weight % of tin to the weight % of rhenium ranges from 0.05 to 0.10 and wherein the weight % is based on the total weight of the catalyst.

Any previously listed weight percent of ruthenium and any previously listed weight percent of rhenium disclosed above may be used in combination with any following amounts of tin ranging from 0.01 to 2.0 weight % or 0.01 to 1.0 weight %, or 0.01 to 0.5 weight % or 0.01 to 0.1 weight % or 0.01 to 0.05 weight %, provided that the ratio of the weight % of tin to the weight % of rhenium ranges from 0.01 to 0.50. Alternatively, any previously listed weight percent of ruthenium and any previously listed weight percent of rhenium disclosed above may be used in combination with any following amounts of tin ranging from 0.01 to 2.0 weight % or 0.01 to 1.0 weight %, or 0.01 to 0.5 weight % or 0.01 to 0.1 weight % or 0.01 to 0.05 weight %, provided that the ratio of the weight % of tin to the weight % of rhenium ranges from 0.05 to 0.10.

In certain embodiments of the present invention the hydrogenation is catalyzed by a catalyst comprising an inert support, 0.5 to 2.0 weight % ruthenium and 0.5 to 3.0 weight % rhenium, wherein the weight % is based on the total weight of the catalyst. Alternatively, the hydrogenation is catalyzed by a catalyst consisting essentially of an inert support, 0.5 to 2.0 weight ruthenium and 0.5 to 3.0 weight % rhenium, wherein the weight % is based on the total weight of the catalyst.

In certain embodiments of the present invention the hydrogenation is catalyzed by a catalyst comprising an inert support, 0.5 to 2.0 weight ruthenium and 0.5 to 2.0 weight % rhenium, wherein the weight % is based on the total weight of the catalyst. Alternatively, the hydrogenation is catalyzed by a catalyst consisting essentially of an inert support, 0.5 to 2.0 weight ruthenium and 0.5 to 2.0 weight % rhenium, wherein the weight % is based on the total weight of the catalyst.

The process of the invention is applicable to carboxylic acids which may be saturated or unsaturated. Mono-, di- or polybasic acids may be employed. Suitably the carboxylic acid may contain from 2 to 20 or 2 to 12 or 2 to 10 or 2 to 8 carbon atoms. The starting carboxylic acid used in the process of this invention may be any organic compound having at least one carboxyl group insofar as any atom or group which prevents or interferes with the relevant reduction is not present in the molecule. Such carboxylic acids usually have a molecular weight of up to about 500.

Suitable monobasic acids include acids having the formula R—COOH wherein R is a substituted or unsubstituted aliphatic, alicyclic, aromatic or araliphatic group, which acids are hydrogenated to alcohols of the formula $RCH_2OH$. Suitably the group R may be a $C_2$ to $C_{20}$ alkyl group or a $C_2$ to $C_{12}$ alkyl group or a $C_2$ to $C_{10}$ alkyl group or a $C_2$ to $C_8$ alkyl group. The R group may be linear or branched.

Examples of suitable carboxylic acids include, but are not limited to, include aliphatic carboxylic acids (e.g. acetic acid, propionic acid, butyric acid, hexanoic acid, octanoic acid, decanoic acid, lauric acid, stearic acid, isobutyric acid, oxalic acid, malonic acid, maleic acid, succinic acid, glutaric acid, adipic acid, glycolic acid, lactic acid, malic acid, oxycaproic acid, pivalic acid, 2-ethylheptanoic acid, monofluoroacetic acid, monochloroacetic acid), aromatic carboxylic acids (e.g. benzoic acid, toluic acid, phthalic acid, naphthoic acid, phenoxybenzoic acid), alicyclic carboxylic acids (e.g. cyclohexanecarboxylic acid), araliphatic carboxylic acids (e.g. phenylacetic acid, 4'-methylphenylacetic acid), etc. Examples of suitable dibasic acids include 1,4-cyclohexanedicarboxylate (CHDA), succinic, glutaric, and maleic acids.

The hydrogenation of the carboxylic acid may be performed within a pressure range of about 400 (2.76 MPa) to 4400 psi (30.3 MPa). In another example, the pressure of the hydrogenation may range from about 500 (3.45 MPa) to about 1000 psi (6.89 MPa).

The hydrogen gas used in the process may comprise fresh gas or a mixture of fresh gas and recycle gas. The hydrogen gas can be a mixture of hydrogen, optional minor amounts of components such as CO and $CO_2$, and inert gases, such as argon, nitrogen, or methane, containing at least about 70 mole % of hydrogen. For example, the hydrogen gas can contain at least 90 mole % or, in another example, at least 97 mole %, of hydrogen. The hydrogen gas may be obtained from any of the common sources well known in the art such as, for example, by partial oxidation or steam reforming of natural gas. Pressure swing absorption can be used if a high purity hydrogen gas is desired. If gas recycle is utilized in the process, then the recycle gas will normally contain minor amounts of one or more products of the hydrogenation reaction which have not been fully condensed in the product recovery stage downstream from the hydrogenation zone. Thus, when using gas recycle in the process of the invention, the gas recycle stream will typically contain a minor amount of an alkanol. Hydrogen is typically fed to the reactor in excess of the stoichiometric quantity and normally is purged from the system. The rate of hydrogen purge is dependent on the temperature and pressure at which the process is operated.

The hydrogenation of the carboxylic acid may be carried out over a temperature range of about 75° to 250° C. Other examples of temperatures for the hydrogenation of the esterification product mixture include about 100 to about 200° C., about 110 to about 150° C., and about 120 to about 150° C.

The hydrogenation reaction may be conducted with a solvent that is capable of dissolving the carboxylic acid. The solvent may a single solvent or a mixture of two or more solvents. The solvent may be inert meaning that it does not substantially react, i.e., less than about 20 wt % or less than about 10 wt % of the solvent reacts, under the hydrogenation reaction conditions. Alternatively, the solvent may be reactive under the hydrogenation reaction conditions to give a reduction product, typically an alcohol. Hydrocarbons and alcohols, such as heptane or ethanol respectively, are typically inert solvents. Ketones and esters may be inert under specific hydrogenation conditions. However, ketones and esters may also be reactive solvents that are reduced to the corresponding alcohols under certain hydrogenation conditions. The solvents may include two or more functional groups. For example, the term "ester" may include diesters or triesters or polyesters. The two or more functional groups may be the same or different.

The hydrogenation of the carboxylic acid may occur without solvent when the carboxylic acid is liquid under the reaction temperatures, typically at temperatures ranging from 100 to 200° C. Alternatively, the hydrogenation of the carboxylic acid occurs in the presence of a solvent. The carboxylic acid may range from 0.1 wt % to 99 wt % and the solvent may range from 1 wt % to 99.9 wt %. Alternatively, carboxylic acid may range from 0.1 wt % to 50 wt % and the solvent may range from 50 wt % to 99.9 wt %. Alternatively, carboxylic acid may range from 0.1 wt % to 25 wt % and the solvent may range from 75 wt % to 99.9 wt %. Alternatively, carboxylic acid may range from 0.1 wt % to 10 wt % and the solvent may range from 90 wt % to 99.9 wt %. Alternatively, carboxylic acid may range from 0.1 wt % to 95 wt % and the solvent may range from 95 wt % to 99.9 wt %. The weight % of the mixtures of solvent and carboxylic acid are based on the total weight of the solvent and the carboxylic acid.

Suitable support materials in all embodiments of the present invention may include, for example, stable metal oxide-based supports or ceramic-based supports. Examples of suitable support materials include, but are not limited to, materials selected from the group consisting of silica, silica/alumina, calcium metasilicate, pyrogenic silica, high purity silica, carbon excluding carbon activated by treatment with a Lewis acid, iron oxide, alumina, alpha-alumina, gamma-alumina, theta-alumina, titanated alumina, silica/aluminas, titania, zirconia, kielsguhr, graphite, aluminum phosphate and mixtures thereof. Preferred support materials include carbon, silica, alumina and mixtures thereof.

The process of the present invention may be carried out in a batch, semi-continuous or continuous mode using conventional chemical processing techniques. In another embodiment of the present invention the process comprises a combination of two or more of batch, semi-continuous or continuous modes. In certain embodiments, the mode of operation may be a continuous process in which the carboxylic acid and solvent mixture is passed over and through one or more fixed beds of catalyst in a "trickle bed" manner and all or a portion of the carboxylic acid is converted to the corresponding alcohol. A portion of the alcohol may be recycled to the feed port of the reactor where it serves as a solvent for the hydrogenation feed materials.

In the drawings and specification, there have been disclosed typical preferred embodiments of the invention and, although specific terms are employed, they are used in a generic and descriptive sense only and not for purposes of limitation, the scope of the invention being set forth in the following claims.

EXAMPLES

Example 1

Bimetallic Ru—Re and Ru—Sn Catalysts

1a. Preparation of Re Promoted Ruthenium Catalyst

The preparation of a Re promoted ruthenium catalyst used an incipient wetness impregnation method. Perrhenic acid solution (65-70 wt % in water) was purchased from Aldrich and used as the rhenium starting material. Distilled and de-ionized water was used to prepare a perrhenic acid impregnation solution.

An alumina supported Ru catalyst sample (15 g, 1/16" spheres, 2% Ru loading, purchased from BASF, SE09079) was charged to a 100 ml glass bottle. Then, 10 g of perrhenic acid aqueous solution (0.05 g of the above mentioned perrhenic acid solution and 9.5 g of distilled and de-ionized water) was drop-wise added to the glass bottle, while the spheres were gently stirred with a spatula. Impregnated spheres were dried at ambient temperature for 4 hours and then at 120° C. in an oven overnight. Finally, the dried spheres were treated in 100 standard cubic centimeters per minute (SCCM) of 10% hydrogen in helium at 200° C. for 2 hours. The nominal Re loading was 0.15%.

1b. Preparation of Sn Promoted Ruthenium Catalyst

The preparation of a Sn promoted ruthenium catalyst used an incipient wetness impregnation method. Tin chloride dihydrate was purchased from Aldrich and used as tin starting material. Distilled and de-ionized water was used as to prepare a tin chloride dihydrate impregnation solution. An alumina supported Ru catalyst sample (15 g, 1/16" spheres, 2% Ru loading, purchased from BASF, SE09079) was charged to a 100 ml glass bottle. Then, 10.15 g of tin chloride aqueous solution (0.03 g $SnCl_2$ dissolved in 10.12 g distilled and de-ionized water) was drop-wise added to the glass bottle, while the spheres were gently stirred with a spatula. Then, impregnated spheres were dried at ambient temperature for 4 hours and then at 120° C. in an oven overnight. Finally, the dried spheres were treated in 100 standard cubic centimeters per minute (SCCM) of 10% hydrogen in helium at 200° C. for 2 hours. The nominal Sn loading was 0.15%.

Similar procedures were used to prepare Ru—Re and Ru—Sn catalysts with loadings of 500 (Example 1b.1), 1000 (Example 1b.2), and 1500 (Example 1b.3) ppm of rhenium and tin, respectively.

The Ru—Re and Ru—Sn catalysts were tested in a batch autoclave by hydrogenation of 3 wt % isobutyric acid in heptane for 4 hours at 800 psi and 123° C. with 3.4 mL (~2.5 g) of catalyst. The rate of acid hydrogenation was measured as the rate of isobutanol generation per hour. Isobutanol and Isobutyric acid were quantified by a wt %-calibrated GC method. The GC method used an Agilent model 68890 GC, or its equivalent, equipped with a DM™ 1701 fused silica capillary column, 30 meters×0.25 mm ID×100 micron thickness. The column temperature conditions were isothermal at 60° C. for 4 minutes, then heated to 120° C. at a rate of 12° C. per minute, then programmed to a final temperature of 240° C. at a rate of 30° C. per minute, then the final temperature of 240° C. was maintained for 3 minutes. The GC was equipped with an FID detector at 250° C. and a split injector set at a temperature of 250° C. with a split ratio of 50:1. The carrier gas was helium at 10 psi back pressure in a constant pressure mode. The neat sample injection size was 0.2 microLiter.

TABLE 1

Acid Reduction Rate Data for FIG. 1

| | Promoter Metal Loading | $k_{acid}$ (1/hr) | |
|---|---|---|---|
| Example | (ppmw) | Re | Sn |
| 1b.1 | 500 | 0.026 | 0.019 |
| 1b.2 | 1000 | 0.049 | 0.012 |
| 1b.3 | 1500 | 0.077 | 0.003 |

FIG. 1 shows that the effect of adding a single promoter to Ru/alumina is very different for Re compared to Sn. Rhenium has the effect of enhancing the acid hydrogenation rate. In contrast, the addition of tin to Ru/alumina slightly decreases the acid hydrogenation rate. Addition of 1500 ppm Re provides more than a three-fold increase in the acid hydrogenation rate compared to a similar catalyst with only 500 ppm Re.

Example 2

Bimetallic Ru—Sn and Ru—Re Catalysts Versus Ru Catalysts

Ru—Re and Ru—Sn bimetallic promoted catalysts were compared to the performance of the unpromoted 2 wt % Ru/alumina system. Catalyst performance was evaluated by reaction in a batch autoclave. A mixture of 3 wt % acid in heptane was hydrogenated at 800 psi and 123 C over 3.4 mL (~2.5 g) of catalyst. Samples were collected hourly and analyzed for acid and isobutanol by a wt %-calibrated GC method. The rate was calculated as the rate of isobutanol production.

Figure 2:
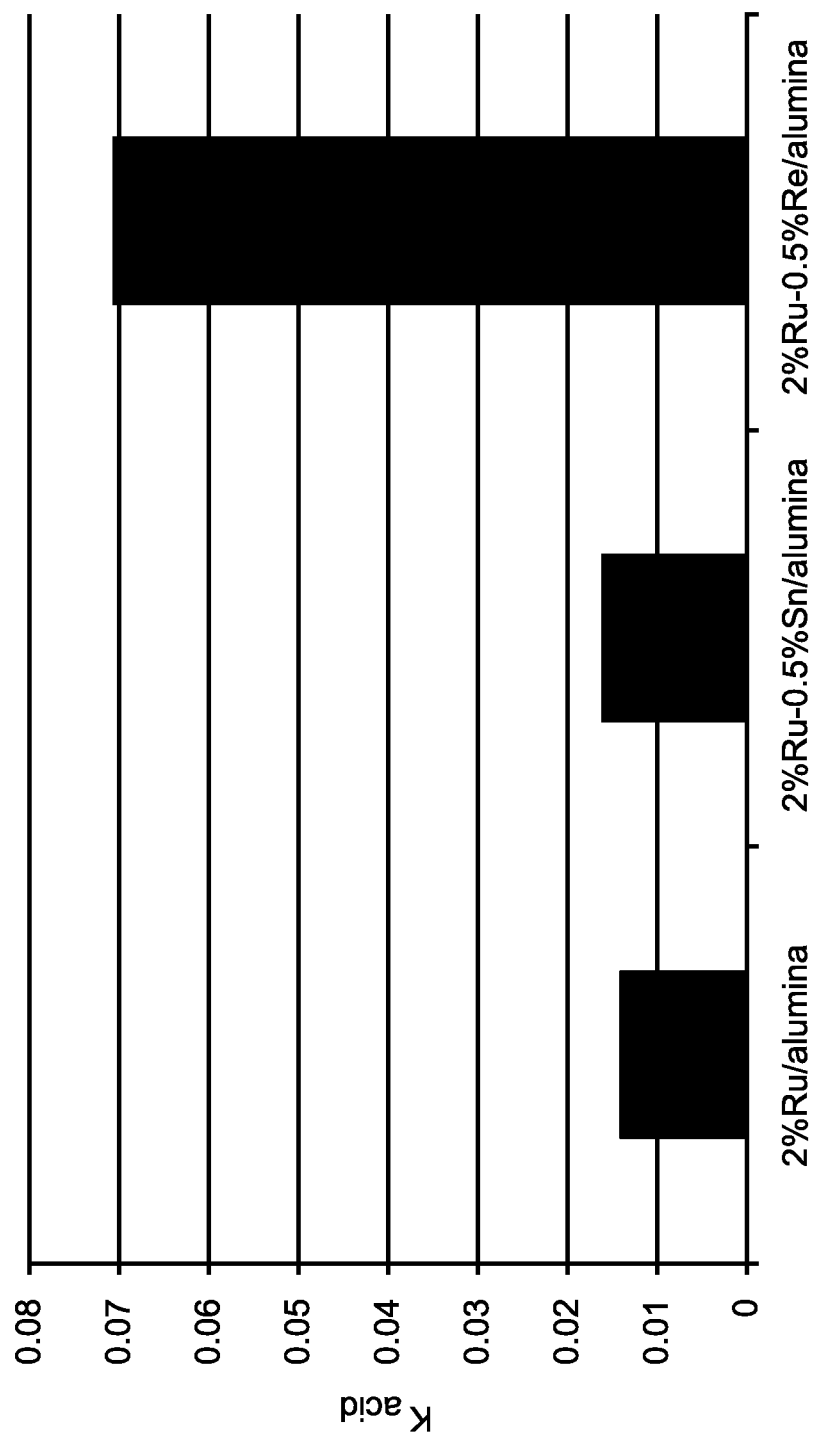
FIG. 2 is a graph showing the carboxylic acid hydrogenation rates for Ru, Ru—Sn, and Ru—Re catalysts.

The acid hydrogenation rates of three catalysts are compared: 2.1) unpromoted Ru/alumina, 2.2) Ru—Sn/alumina, and 2.3) Ru—Re/alumina. As shown in FIG. 2, adding 0.5 wt % Sn to the 2 wt % Ru/alumina catalyst has a negligible effect on the acid hydrogenation rate and the catalyst performance is equivalent to the unpromoted catalyst. In contrast, the addition of 0.5 wt % Re increases the acid hydrogenation rate by a factor of more than 3.

TABLE 2

Acid Reduction Rate Data for FIG. 2

| Example | | $k_{acid}$ (1/hr) |
|---|---|---|
| 2.1 | 2% Ru/alumina | 0.014 |
| 2.2 | 2% Ru—0.5% Sn/alumina | 0.016 |
| 2.3 | 2% Ru—0.5% Re/alumina | 0.071 |

Example 3

Trimetallic Ru—Re—Sn Catalysts

Additional benefit was achieved by combining Ru, Re and Sn in the same catalyst. The catalysts to be evaluated are listed in Table 3. The unpromoted 2 wt % Ru/alumina catalyst is used as the basis for comparison. The unpromoted catalyst is slow for acid hydrogenation so we investigated the addition of chemical promoters (Re and Sn) to the catalyst in order to improve the acid rate. All of these catalysts are prepared on the same support, which is a 1/16" alpha-alumina sphere with 10 m²/g surface area

TABLE 3

Catalysts Compositions

| | Catalyst | Ru Wt % | Re Wt % | Sn Wt % | Sn/Re |
|---|---|---|---|---|---|
| 3.1 | 2% Ru/alumina | 2 | 0 | 0 | |
| 3.2 | 2% Ru—0.5% Re/alumina | 2 | 0.5 | 0 | |
| 3.3 | 2% Ru—0.5% Re—0.025% Sn/alumina | 2 | 0.5 | 0.025 | 0.05 |
| 3.4 | 2% Ru—0.5% Re—0.05% Sn/alumina | 2 | 0.5 | 0.05 | 0.1 |
| 3.5 | 2% Ru—2% Re/alumina | 2 | 2 | 0 | 0 |
| 3.6 | 2% Ru—2% Re—0.1% Sn/alumina | 2 | 2 | 0.1 | 0.05 |
| 3.7 | 2% Ru—2% Re—0.5% Sn/alumina | 2 | 2 | 0.5 | 0.25 |
| 3.8 | 2% Ru—2% Re—1% Sn/alumina | 2 | 2 | 1 | 0.5 |

Figure 3:
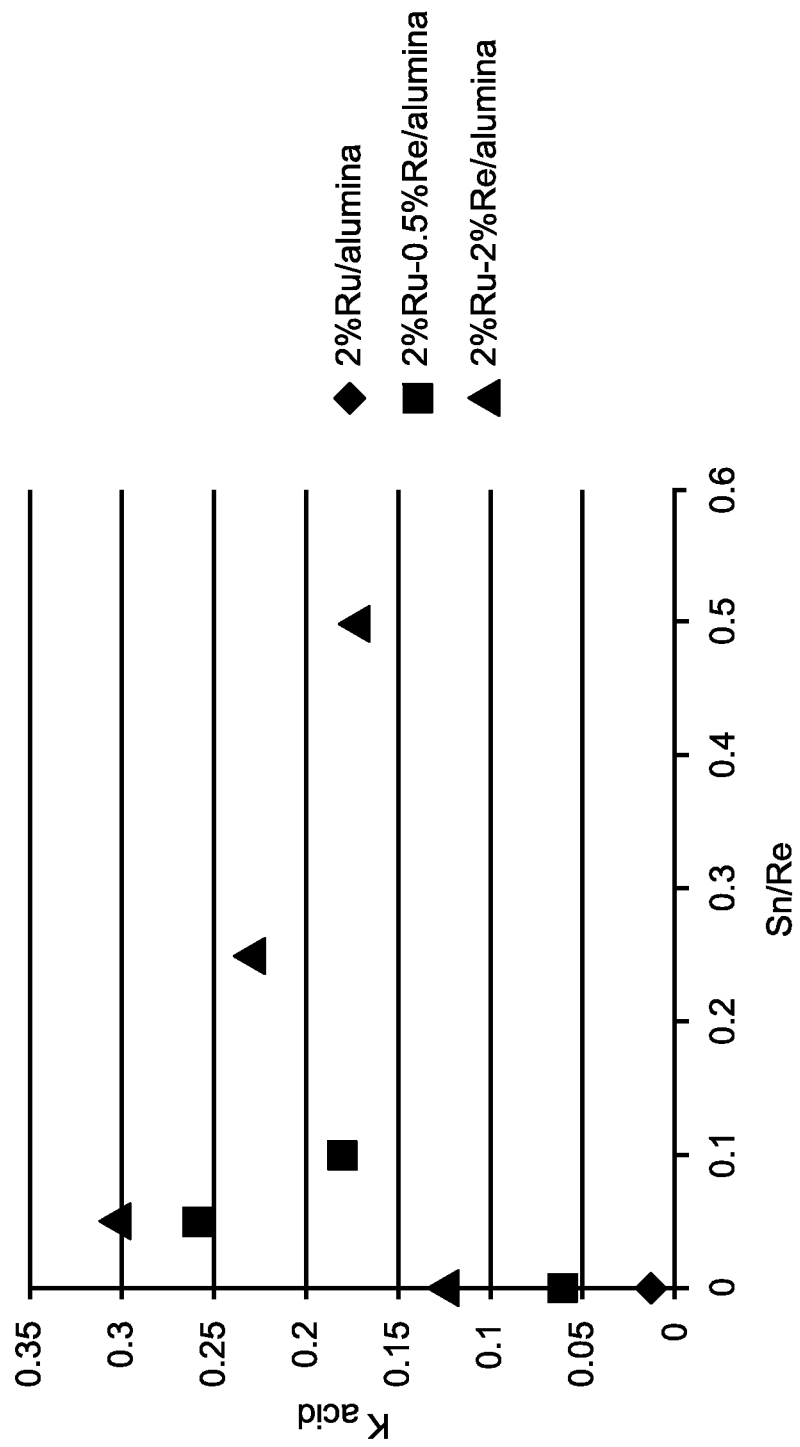
FIG. 3 is a graph showing carboxylic acid hydrogenation rates for Ru and Ru—Re and Ru—Re—Sn catalysts.

The results of the evaluations are shown in FIG. 3. which plots the rate (or rate constant) on the y-axis. (The liquid phase hydrogenation of isobutyric acid is nearly zero-order, therefore the rate and the rate constant are numerically equal.) The ratio of the weight % of Sn to the weight % of Re increases along the x-axis. The rate observed with the standard unpromoted catalyst (diamond) is very low (<0.05). Adding 0.5 wt % or 2 wt % Re to the catalyst increases the acid rate to 0.06 and 0.12, respectively. Further addition of Sn to the Re-promoted catalysts increases the acid hydrogenation rate even further, up to 0.25-0.30 (10-15 times the rate of the unpromoted ruthenium catalyst). Addition of Sn beyond Sn/Re=0.1 appears to diminish the effect.

TABLE 4

Effect of Tin Promoter on Acid Reduction Rates

| Example | | Sn/Re | $k_{acid}$ (1/hr) |
|---|---|---|---|
| 3.1 | 2% Ru/alumina | 0.00 | 0.014 |
| 3.2 | 2% Ru—0.5% Re/alumina | 0.00 | 0.061 |
| 3.3 | 2% Ru—0.5% Re—0.025% Sn/alumina | 0.05 | 0.259 |
| 3.4 | 2% Ru—0.5% Re—0.05% Sn/alumina | 0.10 | 0.180 |
| 3.5 | 2% Ru—2% Re/alumina | 0.00 | 0.126 |
| 3.6 | 2% Ru—2% Re—0.1% Sn/alumina | 0.05 | 0.303 |
| 3.7 | 2% Ru—2% Re—0.5% Sn/alumina | 0.25 | 0.230 |
| 3.8 | 2% Ru—2% Re—1% Sn/alumina | 0.50 | 0.173 |

The Sn/Re ratio is determined by dividing the weight percent of tin promoter by the weight percent of rhenium wherein the weight percents are based on the total weight of the catalyst.

Re and Sn used in combination can increase the acid hydrogenation activity by more than an order of magnitude. Even at a low loading of Re (0.5 wt %), a small addition of Sn enables a significant increase in the observed acid hydrogenation rate. Preferred catalyst compositions include about 2 wt % Ru, about 0.5-2.0 wt % Re and about 0.01-0.03 wt % Sn.

Example 4

Ru—Re—Sn Catalyst Used to Hydrogenate MHCD Acid

Figure 4:
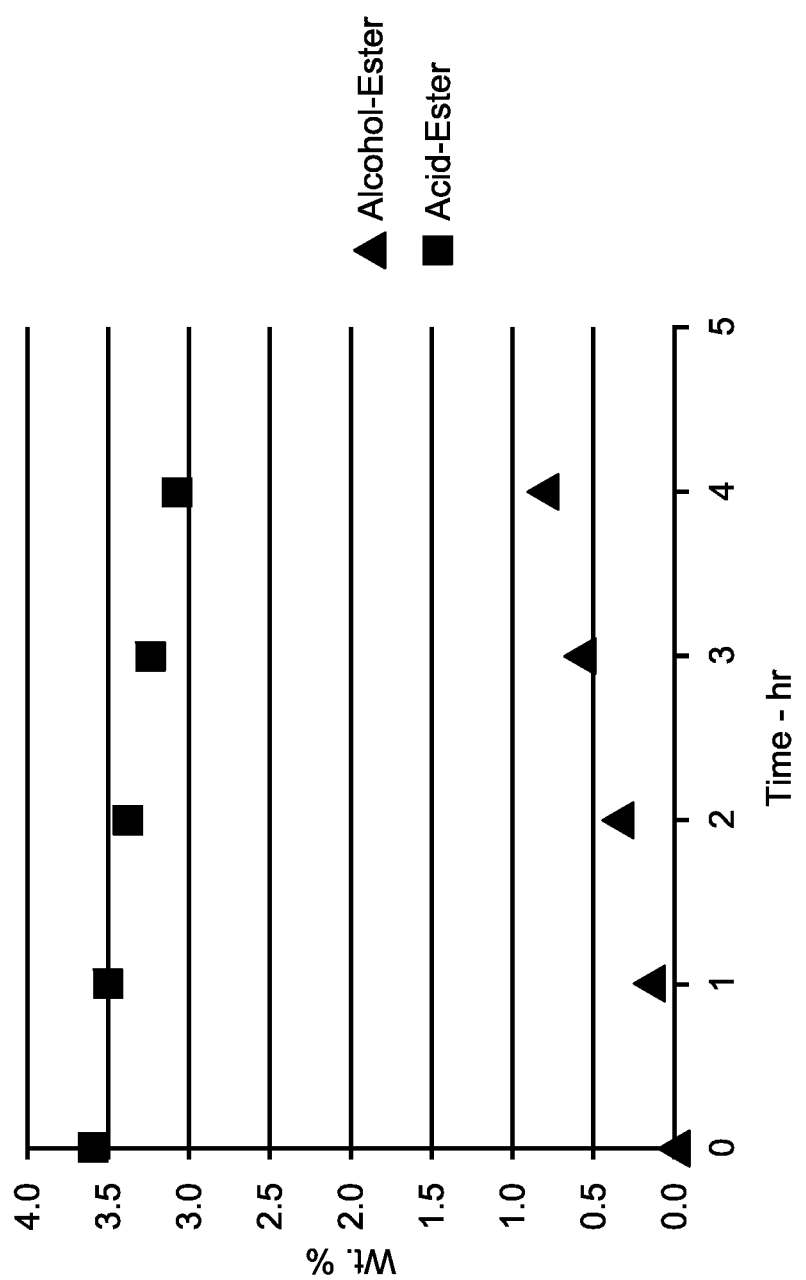
FIG. 4 is a graph showing carboxylic acid hydrogenation rates and alcohol formation rates.

Ru—Re—Sn catalysts are generally useful for hydrogenation of other acids other than isobutyric acid. One example is the hydrogenation of an acid-ester (MHCD) to the corresponding alcohol-ester as depicted in FIG. 4. A catalyst with the composition of 2 wt % Ru-0.5 wt % Re-250 ppm(wt) Sn/alumina was used.

All experiments in this example were performed in batch autoclaves over a temperature range of 110-190° C. and pressure range of 400-4400 psi (2.76 to 30.3 MPa). Acid conversion was observed at all these conditions; however selectivity was lower at the higher temperatures. The principle byproduct was further hydrogenolysis of the alcohol to a methyl group.

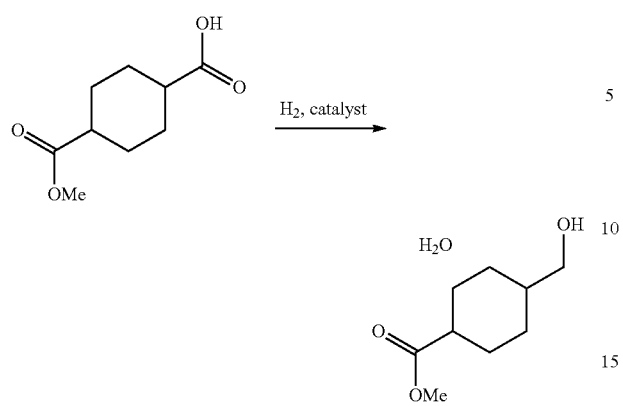

Equation 1 Hydrogenation of an acid-ester MHCD with a Ru—Re—Sn catalyst to generate an alcohol-ester.

Results for all experiments, which start with 3 wt % of the carboxylic acid, are shown in Table 2. For each experiment, the rate refers to the rate of acid disappearance as determined by titration. Representative results of a single experiment 4.7 are shown in FIG. 4, where the concentrations of the acid-ester and alcohol-ester are shown over time.

TABLE 5

The table summarizes the results for several batch experiments. The reported rate is the consumption rate of acid as determined by titration.

| Experiment | T (C.) | P (psi) | DMCD (g) | Catalyst (g) | Rate Acid |
|---|---|---|---|---|---|
| 4.1 | 130 | 400 | 190 | 2.5 | 0.04 |
| 4.2 | 150 | 600 | 190 | 2.5 | 0.25 |
| 4.3 | 170 | 800 | 190 | 2.5 | 0.67 |
| 4.4 | 190 | 1000 | 190 | 2.5 | 1.68 |
| 4.5 | 170 | 400 | 190 | 2.5 | 0.21 |
| 4.6 | 130 | 800 | 190 | 2.5 | 0.19 |
| 4.7 | 130 | 1600 | 190 | 2.5 | 0.42 |
| 4.8 | 130 | 1600 | 190 | 5 | 1.32 |
| 4.9 | 130 | 1600 | 1300 | 34 | 0.50 |
| 4.10 | 130 | 4400 | 1300 | 34 | 0.86 |
| 4.11 | 120 | 3000 | 1300 | 34 | 0.52 |
| 4.12 | 110 | 4400 | 1300 | 34 | 0.33 |
| 4.13 | 110 | 1600 | 1300 | 34 | 0.14 |
| 4.14 | 120 | 3000 | 1300 | 34 | 0.44 |
| 4.15 | 130 | 1600 | 190 | 5 | 0.65 |
| 4.16 | 130 | 1600 | 190 | 5 | 0.59 |
| 4.17 | 130 | 1600 | 190 | 10 | 0.76 |
| 4.18 | 130 | 1600 | 190 | 15 | 1.07 |

The rate in Table 5 is expressed as the change in total acid number per hour.

TABLE 6

Data for FIG. 4

| Time (hr) | Alcohol-Ester (Wt %) | Acid (Wt %) |
|---|---|---|
| 0 | 0.00 | 3.60 |
| 1 | 0.15 | 3.50 |
| 2 | 0.35 | 3.39 |
| 3 | 0.58 | 3.25 |
| 4 | 0.81 | 3.07 |

Examples 5-10

Ru—Re—Sn Catalyst Used to Hydrogenate Carboxylic Acids in a Continuous Unit

Several carboxylic acids in isobutyl isobutyrate were hydrogenated under continuous flow conditions in a trickle bed reactor. The initial acid concentration was 0.34-0.40 M in these experiments. The reactor was a section of schedule 40 304L stainless steel pipe (75 inches in length, 1.5 inch diameter). The reactor was charged with 490 mL of 5 mm soda lime glass beads, 405 mL of catalyst and 1200 mL of additional glass beads at the top of the reactor. Temperature was measured at the top and bottom of the catalyst bed. A portion of the reactor effluent (16 L) was mixed with the feed and returned to the reactor. The results demonstrate that the Ru/Re/Sn catalyst is effective in hydrogenating various carboxylic acids under continuous flow conditions.

Example 5

A mixture of 4.22 wt % pivalic acid in isobutyl isobutyrate was added to the reactor system containing 2 wt % Ru-0.5 wt % Re-0.025 wt % Sn on alumina catalyst at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of pivalic acid (2,2-dimethylpropanoic acid) was 45.0% (0.562 mmol/g-hr).

Example 6

A mixture of 5.91 wt % 2-ethylhexanoic acid in isobutyl isobutyrate was added to the reactor system containing 405 mL of a 2 wt % Ru-0.5 wt % Re-0.025 wt % Sn on alumina at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of 2-ethylhexanoic acid was 19.9% (0.246 mmol/g-hr).

Example 7

A mixture of 3.23 wt % propionic acid in isobutyl isobutyrate was added to the reactor system containing 405 mL of a 2 wt % Ru-0.5 wt % Re-0.025 wt % Sn on alumina at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of propionic acid was 58.9% (0.787 mmol/g-hr).

Example 8

A mixture of 4.08 wt % isobutyric acid in isobutyl isobutyrate was added to the reactor system containing 405 mL of a 2 wt % Ru-0.5 wt % Re-0.025 wt % Sn on alumina at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of isobutyric acid was 52.8% (0.738 mmol/g-hr).

Example 9

A solution of 18.0 wt % 2,2,4,4-tetramethylcyclobutane-1,3-dione and 3.90 wt % isobutyric acid in isobutyl isobutyrate was added to the reactor system containing 405 mL of a 2 wt % Ru-0.5 wt % Re-0.025 wt % Sn on alumina catalyst at a rate of 20 mL/min. The pressure at the top of the reactor was maintained at 500 psig and the temperature at the top of the catalyst bed was 128° C. These conditions were maintained for 24 hours. The average conversion of the dione was 98.4%. 2,2,4,4-Tetramethylcyclobutane-1,3-diol (16.5 wt %) was obtained at a rate of 24.8 lb/ft$^3$ catalyst/hr (3.50 mmol/g/hr). The average conversion of isobutyric acid was 44.4% (0.592 mmol/g-hr).

Example 10

A mixture of 4.17 wt % isobutyric acid in isobutyl isobutyrate was added to the reactor system containing 405 mL of a 2 wt % Ru-0.25 wt % Re-0.0125 wt % Sn catalyst at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of isobutyric acid was 40.2% (0.573 mmol/g-hr).

Example 10.1

A mixture of 4.00 wt % isobutyric acid in isobutyl isobutyrate was added to the reactor system containing 405 mL of a 2 wt % Ru-0.5 wt % Re on alumina catalyst at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of isobutyric acid was 31.6% (0.429 mmol/g-hr).

Comparative Example 1

A mixture of 4.00 wt % isobutyric acid in isobutyl isobutyrate was added to the reactor system containing 405 mL of a 2 wt % Ru on alumina catalyst at a rate of 20 mL/min. The pressure at the top of the reactor was maintained at 500 psig (3.45 MPa) and the temperature at the top of the catalyst bed was 128 degrees C. These conditions were maintained for 24 hours. The average conversion of isobutyric acid was 7.6% (0.104 mmol/g-hr).

Comparative Examples 2-7, Examples 11-31

A number of autoclave runs were made with 2 wt % Ru, 2 wt % Ru-0.5 wt Re, 2 wt % Ru-1 wt % Re, 2 wt % Ru-2 wt % Re and 2 wt % Ru-0.5 wt % Re-250 ppm(wt) Sn. All of these catalysts are prepared on the same support, which is a $\frac{1}{16}$" alpha-alumina sphere with 10 m$^2$/g surface area. Each catalyst was evaluated in four different reactions in which the conversion of either isobutyric acid (HOiBu) or acetic (HOAc) was measured after three hours at 130° C. and 500 psig (3.45 MPa) hydrogen. The four reactions were hydrogenation of isobutyric acid in isobutyl isobutyrate (IBIB); hydrogenation of methyl isopropyl ketone (MIPK) in the presence of 5% isobutyric acid; hydrogenation of MIPK in the presence of 5% acetic acid; and hydrogenation of acetic acid in ethyl acetate. Others examples are included in which 5% of a carboxylic acid is hydrogenated in the presence of a reactive solvent such as a ketone or a non-reactive solvent. The general procedure is as follows: A 300 mL autoclave was charged with 10 g of catalyst in a basket, 7 grams of a carboxylic acid, and 133 g of non-reactive solvent or ketone. The autoclave was closed, purged with hydrogen three times, and then the pressure was increased to 500 psig (3.45 MPa) with hydrogen and held for 3 hr at 130° C. The conversion of acid and ketone was measured by GC analysis. The results are summarized in Table 7.

TABLE 7

Conversion of Carboxylic Acids to Alcohols

| Run | Catalyst | Acid | Ketone | Solvent | Acid conv | Ketone conv |
|---|---|---|---|---|---|---|
| Comparative Example 2 | 2% Ru on Al2O3 | 5% HOiBu | | IBIB | 5.1% | |
| Comparative Example 3 | 2% Ru on Al2O3 | 5% HOiBu | MIPK | | 14.7% | >99% |
| Comparative Example 4 | 2% Ru on Al2O3 | 5% HOAc | MIPK | | 24.8% | >99% |
| Comparative Example 5 | 2% Ru on Al2O3 | 5% HOAc | | EtOAc | 1.1% | |
| Comparative Example 6 | 2% Ru on Al2O3 | 5% HOBu | | NBNB | 1.7% | |
| Comparative Example 7* | 2% Ru on Al2O3 | 5% Benzoic Acid | | TXIB | 9.4% | |
| Example 11 | 2% Ru—0.5% Re on Al2O3 | 5% HOiBu | | IBIB | 34.0% | |
| Example 12 | 2% Ru—0.5% Re on Al2O3 | 5% HOiBu | MIPK | | 24.3% | >99% |
| Example 13 | 2% Ru—0.5% Re on Al2O3 | 5% HOAc | MIPK | | 27.0% | >99% |
| Example 14 | 2% Ru—0.5% Re on Al2O3 | 5% HOAc | | EtOAc | 17.7% | |
| Example 15 | 2% Ru—1% Re on Al2O3 | 5% HOiBu | | IBIB | 44.4% | |
| Example 16 | 2% Ru—1% Re on Al2O3 | 5% HOiBu | MIPK | | 31.9% | >99% |
| Example 17 | 2% Ru—1% Re on Al2O3 | 5% HOAc | MIPK | | 37.3% | >99% |
| Example 18 | 2% Ru—1% Re on Al2O3 | 5% HOAc | | EtOAc | 41.1% | |
| Example 19 | 2% Ru—2% Re on Al2O3 | 5% HOiBu | | IBIB | 29.9% | |
| Example 20 | 2% Ru—2% Re on Al2O3 | 5% HOiBu | MIPK | | 28.4% | >99% |
| Example 21 | 2% Ru—2% Re on Al2O3 | 5% HOAc | MIPK | | 36.2% | >99% |
| Example 22 | 2% Ru—2% Re on Al2O3 | 5% HOAc | | EtOAc | 32.8% | |
| Example 23 | 2% Ru—0.5% Re—0.025% Sn on Al2O3 | 5% HOiBu | | IBIB | 67.6% | |
| Example 24 | 2% Ru—0.5% Re—0.025% Sn on Al2O3 | 5% HOiBu | MIPK | | 50.0% | >99% |

TABLE 7-continued

Conversion of Carboxylic Acids to Alcohols

| Run | Catalyst | Acid | Ketone | Solvent | Acid conv | Ketone conv |
|---|---|---|---|---|---|---|
| Example 25 | 2% Ru—0.5% Re—0.025% Sn on Al2O3 | 5% HOAc | MIPK | | 43.9% | >99% |
| Example 26 | 2% Ru—0.5% Re—0.025% Sn on Al2O3 | 5% HOAc | | EtOAc | 48.5% | |
| Example 27 | 2% Ru—0.5% Re—0.025% Sn on Al2O3 | 5% HOiBu | | iBuOH | 43.1% | |
| Example 28 | 2% Ru—0.5% Re—0.025% Sn on Al2O3 | 5% HOiBu | DIPK | | 48.8% | >99% |
| Example 29 | 2% Ru—0.5% Re—0.025% Sn on Al2O3 | 5% pivalic acid | | IBIB | 36.1% | |
| Example 30 | 2% Ru—0.5% Re—0.025% Sn on Al2O3 | 5% HOBu | | NBNB | 34.6% | |
| Example 31** | 2% Ru—0.5% Re—0.025% Sn on Al2O3 | 5% Benzoic Acid | | TXIB | 28.6% | |

*99.3% conversion of benzoic acid to cyclohexanecarboxylic acid (CCA) and 9.4% conversion of CCA to products
**99.1% conversion of benzoic acid to CCA and 28.6* conversion of CCA to products a. Hydrogenation of isobutyric acid in isobutyl isobutyrate (IBIS) (Comp Ex 2, Ex 11, Ex 15, Ex 19, Ex 23)

Isobutyric acid conversion increased from 5% with the unpromoted catalyst to 30-44% with the Re promoted ruthenium catalyst and to 67% with the Re/Sn promoted ruthenium catalyst.

b. Hydrogenation of MIPK (methyl isopropyl ketone) in the presence of 5% isobutyric acid (Comp Ex 3, Ex 12, Ex 16, Ex 20, Ex 24)

MIPK conversion was >99% in all examples. Isobutyric acid conversion increased as the amount of Re promoted increased on the ruthenium catalyst. The Ru—Re—Sn system was again the most active toward acid hydrogenation.

c. Hydrogenation of MIPK in the presence of 5% acetic acid (Comp Ex 4, Ex 13, Ex 17, Ex 21, Ex 25)

The Ru—Re—Sn was the most active towards acid hydrogenation. Re modified ruthenium catalysts were more active than the Ru catalyst. However there was only minimal difference between the 2 wt % Ru catalyst and the 2 wt % Ru-0.5% Re system (25% vs. 27% conversion of acid.) MIPK conversion was again >99%.

d. Hydrogenation of acetic acid in ethyl acetate (Comp Ex 5, Ex 14, Ex 18, Ex 22, Ex 26)

The Ru—Re—Sn catalyst gave the highest conversion of acid. The Re modified ruthenium catalysts exhibited greater activity than the unmodified ruthenium catalyst.

e. Hydrogenation of butyric acid in n-butyl n-butyrate (NBNB) (Comp Ex 6 and Ex 30)

The Ru—Re—Sn catalyst was greater than 10 times more active than the Ru catalyst toward conversion of the acid to products.

f. Hydrogenation of benzoic acid in 2,2,4-trimethyl-1,3-pentanediol diisobutyrate (TXIB) (Comp Ex 7 and Ex 31)

Both the Ru catalyst and the Ru—Re—Sn catalyst converted benzoic acid to cyclohexanecarboxylic acid in greater than 99% conversion. However, the Ru—Re—Sn catalyst was three times more active in converting cyclohexanecarboxylic acid to alcohol.

The invention claimed is:

1. An anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst comprising:
 (a) an inert support,
 (b) 0.5 to 2.0 weight % ruthenium,
 (c) 0.5 to 3.0 weight % rhenium, and
 (d) 0.01 to 3.0 weight % tin,
wherein the ratio of weight % of tin to the weight % of rhenium ranges from 0.01 to 0.50, and
wherein the weight % is based on the total weight of the catalyst.

2. The process according to claim 1 wherein the solvent is selected from the group consisting ketones, esters, hydrocarbons, alcohols or mixtures thereof.

3. The process according to claim 1 wherein the solvent is inert to hydrogenation.

4. The process according to claim 1 wherein the solvent forms a hydroxyl containing compound during the hydrogenation process.

5. The process according to claim 4 where in the solvent comprises a ketone, ester or mixture thereof.

6. The process according to claim 1 wherein the pressure ranges from 500 to 1000 psi.

7. The process according to claim 1 wherein the tin ranges from 0.01 to 0.03 wt % and wherein the weight % is based on the total weight of the catalyst.

8. The process according to claim 1 wherein the rhenium ranges from 0.5 to 2.0 weight % and wherein the weight % is based on the total weight of the catalyst.

9. The process according to claim 1 wherein the tin ranges from 0.01 to 0.03 wt %, wherein the rhenium ranges from 0.5 to 2.0 weight % and wherein the weight % is based on the total weight of the catalyst.

10. The process according to claim 1 wherein the solvent ranges from about 90 to 99.9 wt. % and the carboxylic acid ranges from about 0.1 to about 10 wt %, wherein the weight % is based on the total weight of the solvent and the carboxylic acid.

11. An anhydrous liquid phase process for making an alcohol from a carboxylic acid, the process comprising contacting a carboxylic acid with hydrogen in the presence of a heterogeneous catalyst and a solvent at a temperature ranging from 100° C. to 200° C. and pressure ranging from 400 to 4000 psi to form the alcohol, the catalyst comprising:
 (a) an inert support,
 (b) 0.5 to 2.0 weight % ruthenium,
 (c) 0.5 to 3.0 weight % rhenium, wherein the weight % is based on the total weight of the catalyst.

12. The process according to claim 11 wherein the solvent is selected from the group consisting ketones, esters, hydrocarbons, alcohols or mixtures thereof.

13. The process according to claim 11 wherein the solvent is inert to hydrogenation.

14. The process according to claim 11 wherein the solvent forms a hydroxyl containing compound during the hydrogenation process.

15. The process according to claim 14 where in the solvent comprises a ketone, ester or mixture thereof.

16. The process according to claim 11 wherein the pressure ranges from 500 to 1000 psi.

17. The process according to claim 11 wherein the rhenium ranges from 0.5 to 2.0 weight % and wherein the weight % is based on the total weight of the catalyst.

18. The process according to claim 11 wherein the rhenium ranges from 0.5 to 2.0 weight % and wherein the weight % is based on the total weight of the catalyst.

19. The process according to claim 11 wherein the solvent ranges from about 90 to 99.9 wt. % and the carboxylic acid ranges from about 0.1 to about 10 wt %, wherein the weight % is based on the total weight of the solvent and the carboxylic acid.

20. The process according to claim 1, wherein the ratio of weight % of tin to the weight % of rhenium ranges from 0.05 to 0.10.

* * * * *